US010188538B2

(12) United States Patent
Eller et al.

(10) Patent No.: US 10,188,538 B2
(45) Date of Patent: Jan. 29, 2019

(54) HYBRID TRIGGER WIRE FOR ENDOGRAFTS

(71) Applicant: Cook Medical Technologies LLC, Bloomington, IN (US)

(72) Inventors: Derek Eller, Bloomington, IN (US); Saylon Lukas, Cincinnati, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 189 days.

(21) Appl. No.: 14/984,048

(22) Filed: Dec. 30, 2015

(65) Prior Publication Data

US 2017/0189212 A1    Jul. 6, 2017

(51) Int. Cl.
| | | |
|---|---|---|
| A61F 2/95 | (2013.01) | |
| A61F 2/07 | (2013.01) | |
| A61F 2/844 | (2013.01) | |
| A61F 2/954 | (2013.01) | |

(52) U.S. Cl.
CPC .................. *A61F 2/95* (2013.01); *A61F 2/07* (2013.01); *A61F 2/844* (2013.01); *A61F 2/954* (2013.01); *A61F 2002/075* (2013.01); *A61F 2002/9511* (2013.01)

(58) Field of Classification Search
CPC .... A61F 2/95; A61F 2/844; A61F 2/07; A61F 2002/9511; A61F 2002/075; A61F 2/954
See application file for complete search history.

(56) References Cited

U.S. PATENT DOCUMENTS

| | | |
|---|---|---|
| 5,405,378 A | 4/1995 | Strecker |
| 5,509,902 A | 4/1996 | Raulerson |
| 5,873,906 A | 2/1999 | Lau et al. |
| 6,302,891 B1 | 10/2001 | Nadal |
| 6,352,561 B1 | 3/2002 | Leopold et al. |
| 6,371,979 B1 | 4/2002 | Beyar et al. |
| 6,607,539 B1 | 8/2003 | Hayashi et al. |

(Continued)

FOREIGN PATENT DOCUMENTS

| | | |
|---|---|---|
| EP | 0664107 A1 | 7/1995 |
| WO | WO 2003/034948 A1 | 5/2003 |

(Continued)

OTHER PUBLICATIONS

Extended European Search Report for corresponding EP 16275178, dated May 10, 2017, 7 pages.

(Continued)

*Primary Examiner* — Darwin Erezo
*Assistant Examiner* — Erich Herbermann
(74) *Attorney, Agent, or Firm* — Brinks Gilson & Lione

(57) ABSTRACT

An endovascular prosthesis delivery system is disclosed. The system comprises: an inner cannula; a prosthesis releasably secured to the inner cannula, the prosthesis having a radially-inwardly contracted delivery configuration and a radially-expanded deployed configuration, wherein the prosthesis comprises at least two suture loops secured to an outer surface of the prosthesis and circumferentially spaced from each other; a releasable trigger wire extending along at least a portion of the length of the prosthesis, wherein the releasable trigger wire is wound around at least a portion of the inner cannula and wherein the releasable trigger wire engages at least one of the at least two suture loops to retain the prosthesis in the radially-inwardly contracted delivery configuration.

20 Claims, 7 Drawing Sheets

(56) References Cited

U.S. PATENT DOCUMENTS

| | | | |
|---|---|---|---|
| 6,648,911 B1 | 11/2003 | Sirhan et al. | |
| 7,101,390 B2 | 9/2006 | Nelson | |
| 8,377,113 B2 | 2/2013 | Hartley et al. | |
| 8,728,148 B2 | 5/2014 | Roeder et al. | |
| 8,864,808 B2 | 10/2014 | Greenberg et al. | |
| 8,926,686 B2 | 1/2015 | King | |
| 2004/0106974 A1 | 6/2004 | Greenberg et al. | |
| 2004/0243215 A1 | 12/2004 | Nelson | |
| 2006/0014836 A1 | 1/2006 | Chen et al. | |
| 2007/0043425 A1 | 2/2007 | Hartley et al. | |
| 2010/0049294 A1* | 2/2010 | Zukowski | A61F 2/954 623/1.11 |
| 2012/0172965 A1* | 7/2012 | Kratzberg | A61F 2/962 623/1.12 |
| 2013/0116773 A1* | 5/2013 | Roeder | A61F 2/07 623/1.15 |
| 2013/0289713 A1* | 10/2013 | Pearson | A61F 2/07 623/1.35 |
| 2014/0180386 A1* | 6/2014 | Huser | A61F 2/966 623/1.12 |
| 2014/0277350 A1 | 9/2014 | Melsheimer | |
| 2016/0184118 A1 | 6/2016 | Faber et al. | |

FOREIGN PATENT DOCUMENTS

| | | |
|---|---|---|
| WO | WO 2004/017868 A1 | 3/2004 |
| WO | WO 2007/035895 A2 | 3/2007 |
| WO | WO 2008/140796 A1 | 11/2008 |

OTHER PUBLICATIONS

Examination Report for corresponding EP Application No. 16275178.8, dated May 30, 2018, 6 pages.

* cited by examiner

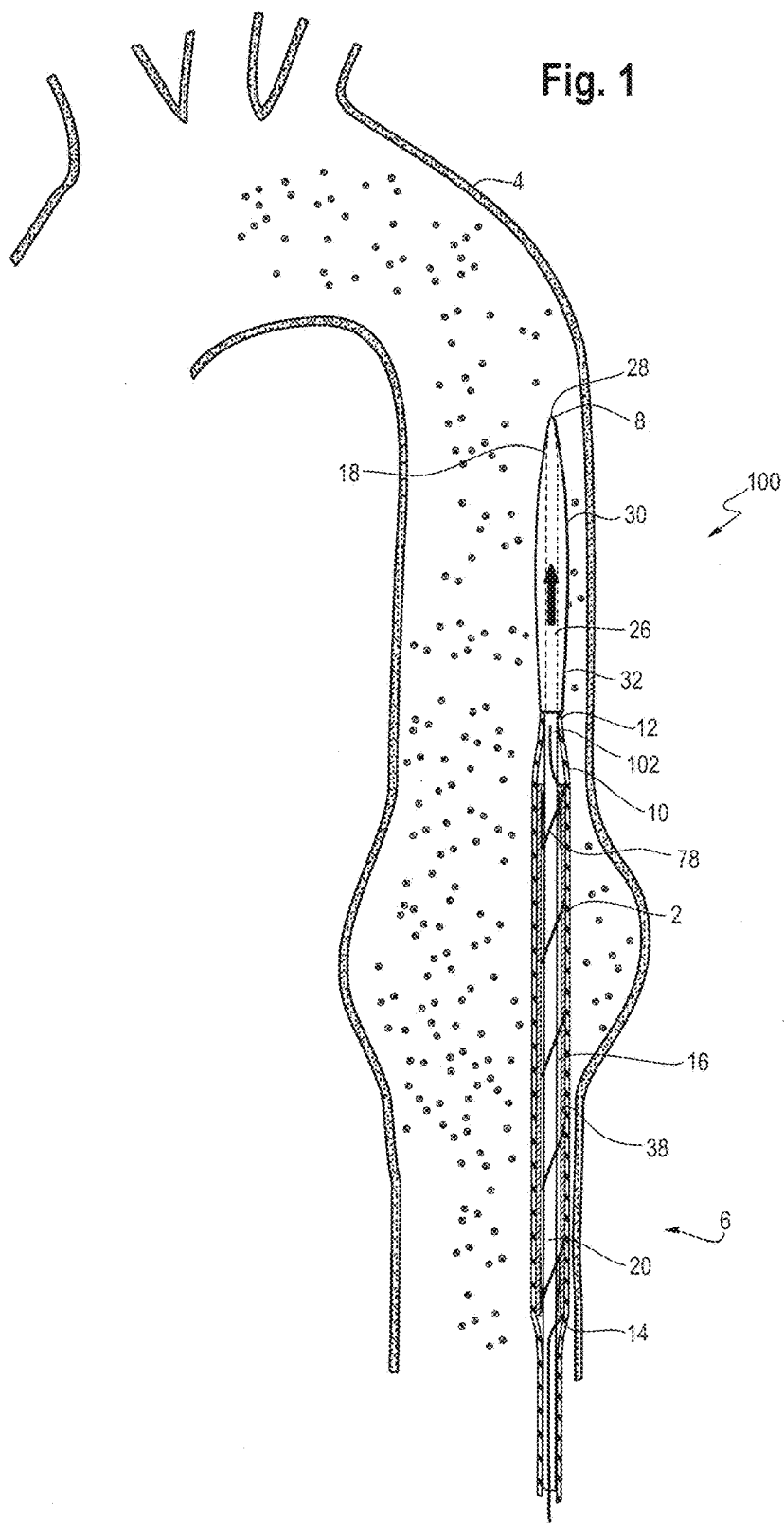

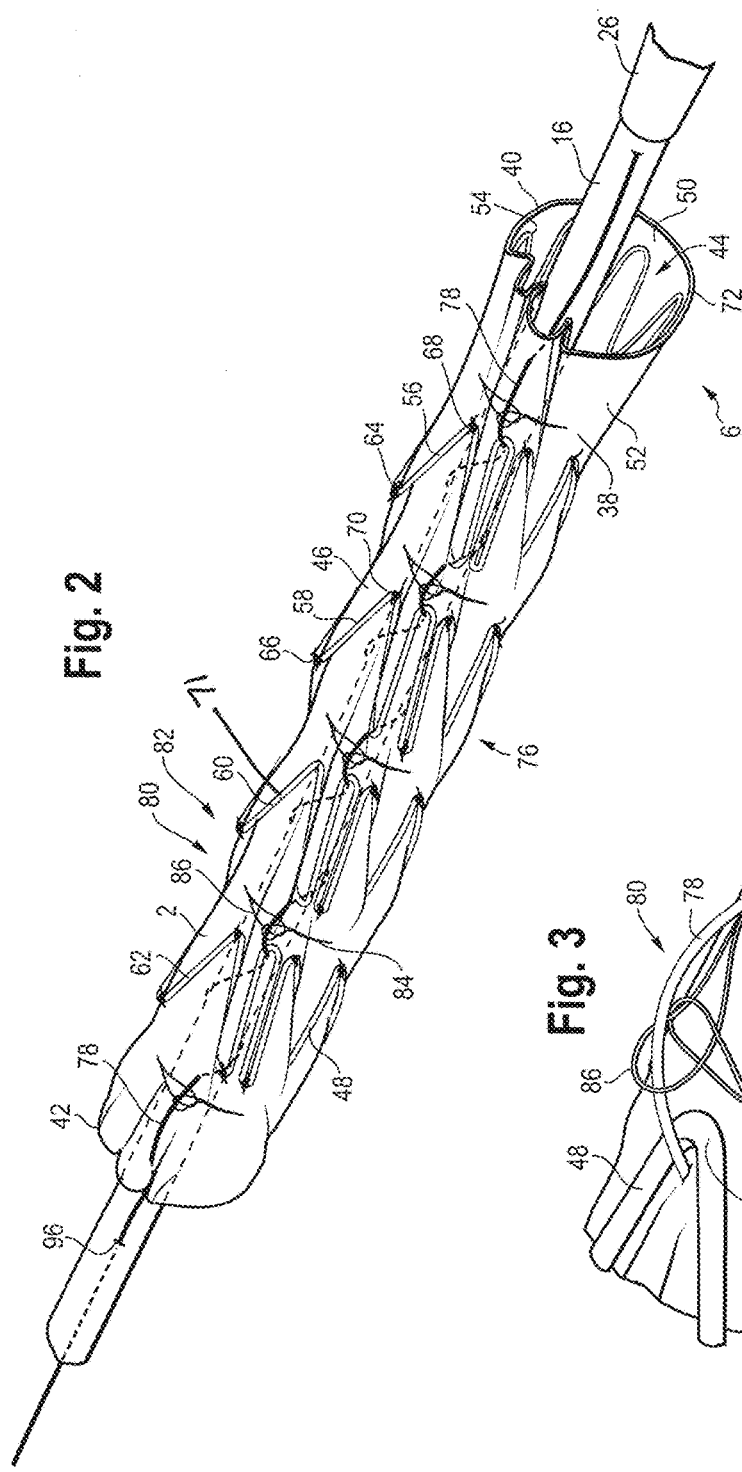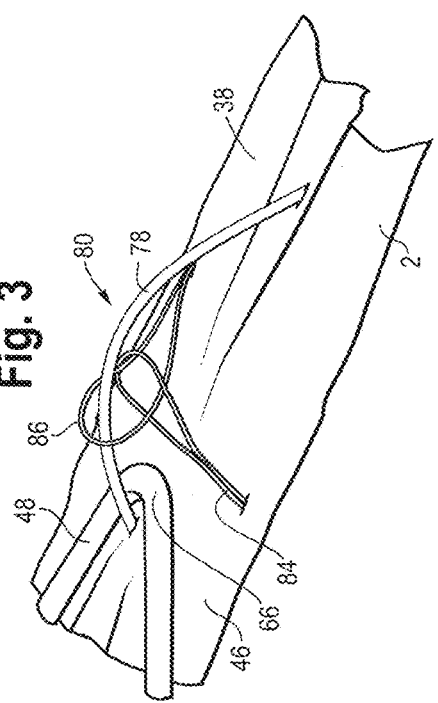

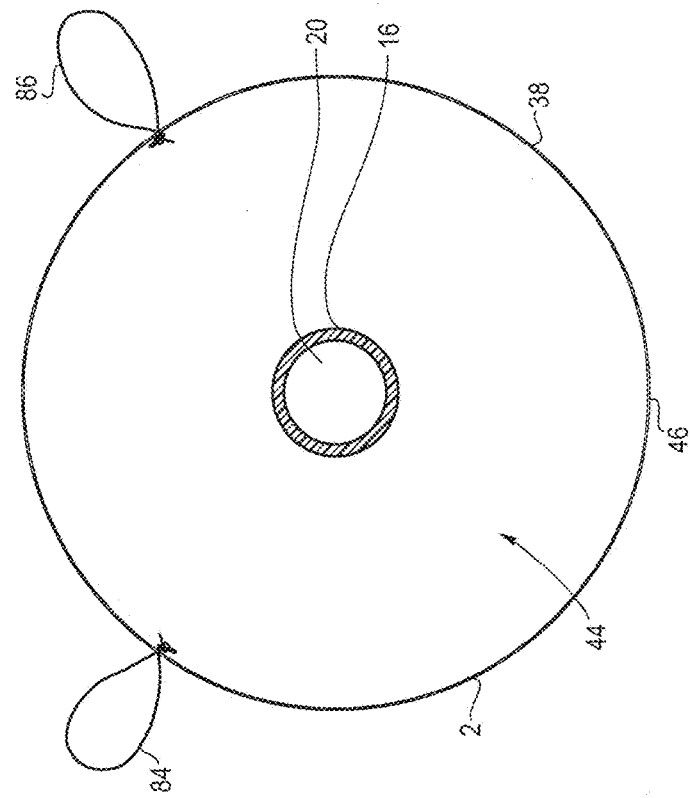
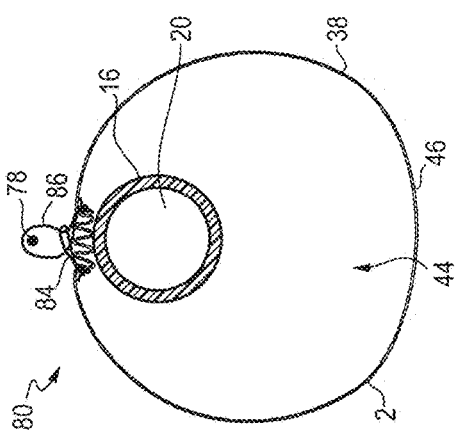

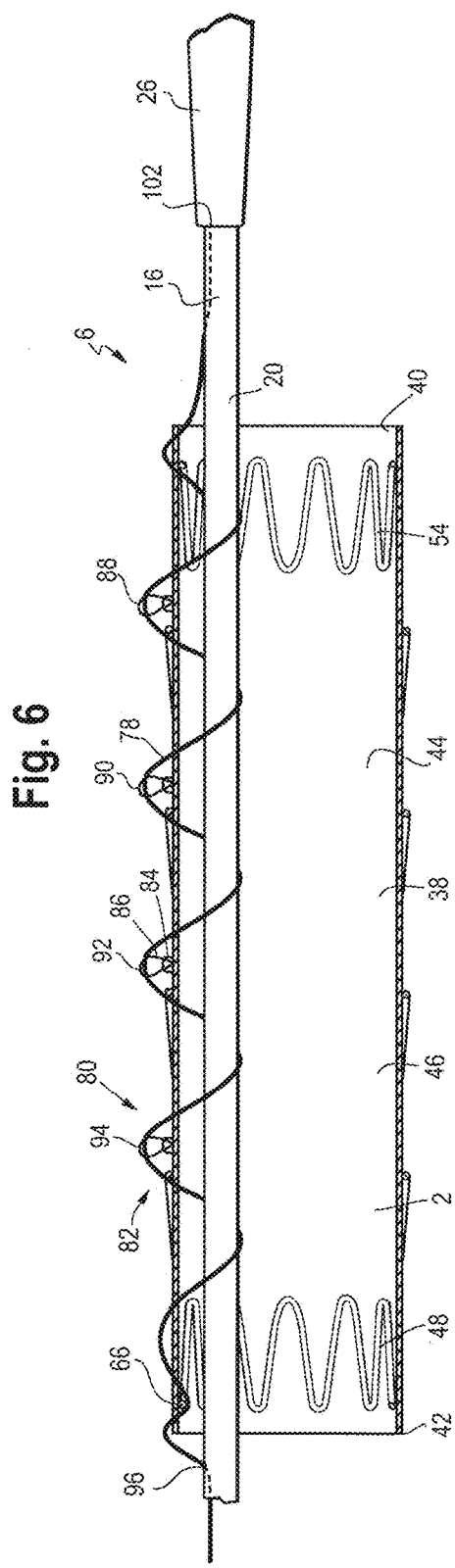

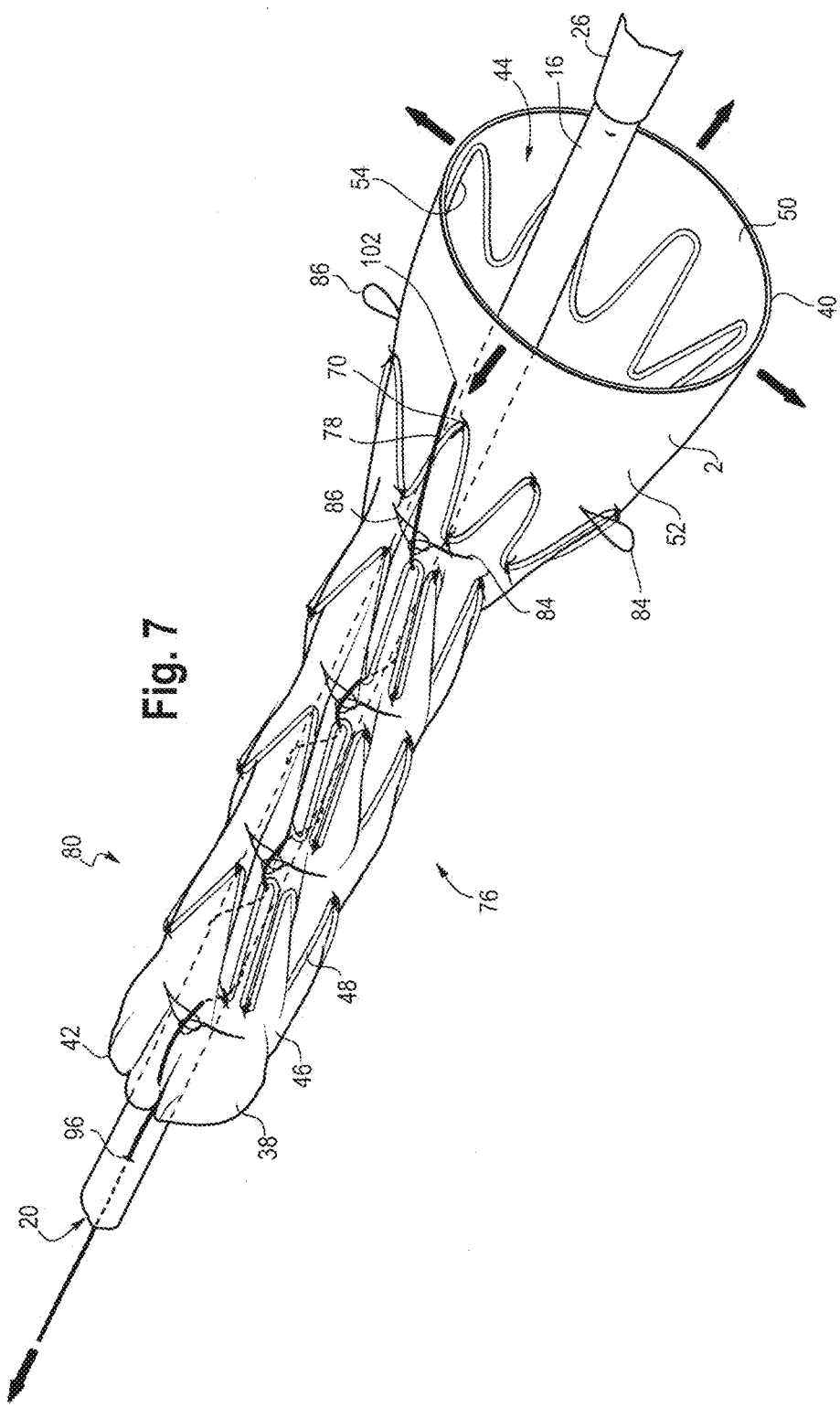

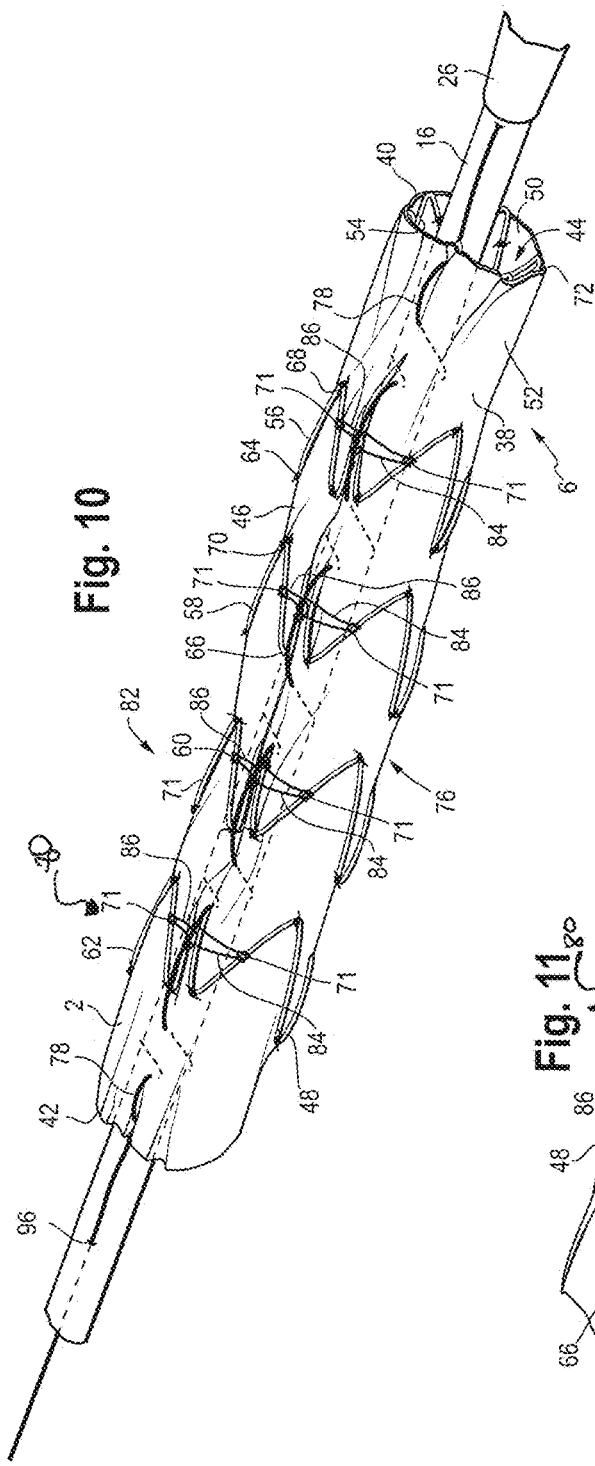
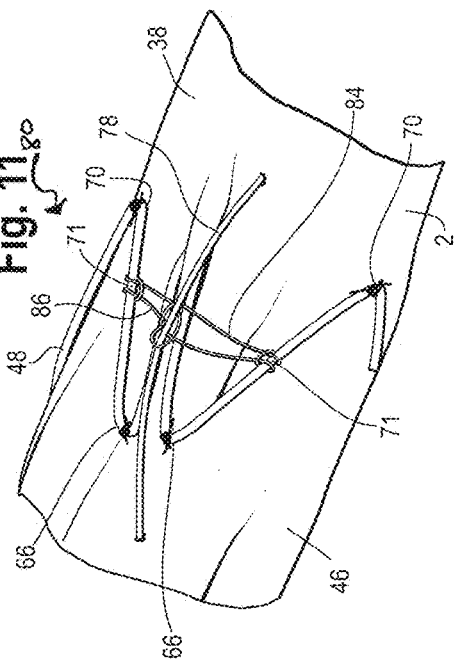

HYBRID TRIGGER WIRE FOR ENDOGRAFTS

TECHNICAL FIELD

This disclosure relates to a medical device. More particularly, it relates to apparatus and methods for deploying endoluminal prostheses in a body vessel, duct, or lumen.

BACKGROUND

Endoluminal prostheses may be inserted into a body lumen such as an anatomical vessel or duct for various purposes. Prostheses may maintain or restore patency in a formerly blocked or constricted passageway or they may be used for different procedures. For example, a prosthesis may include one or more stents placed in or about a graft, and the stents may hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be self-expanding or mechanically-expandable or they may have characteristics of both. Preferably, stents may be delivered to a target site in a compressed configuration and subsequently expanded by removing a delivery sheath, removing trigger wires, releasing diameter-reducing ties and/or employing manual stent-expansion techniques. Accurate positioning of stent grafts in a main artery is desirable for a number of reasons such as to avoid occlusion of branch arteries extending from the main artery. Once released from a delivery device, a stent graft with self-expanding stents will assume a position against the vessel wall, making any subsequent repositioning difficult.

Deployment devices are commonly used to position and deploy prostheses, particularly those including self-expanding stents, within various body lumens. In some deployment devices, one or more trigger wires may be used to assist surgeons with the task of positioning stent grafts even after initial release from a deployment device as described herein. In particular, trigger wires can be used to fully or at least partially restrain a prosthesis in a particular position on the deployment device or to restrain one or more self-expanding stents of the prosthesis in a compressed state to facilitate positioning of the stent graft. One such type of trigger wire may be used with one or more diameter reducing ties, which holds two points on the circumference of a graft closer together, effectively reducing the diameter of the graft. The ties are then released, usually by removal of the trigger wire, once the graft is in its intended position. Another such type of trigger wire, which may be referred to herein as a "spiral wire," secures the graft to a cannula running through the graft lumen. The spiral wire may increase the accuracy of rotational alignment during deployment.

SUMMARY

In one example, an endovascular prosthesis delivery system is described. The delivery system comprises an inner cannula; a prosthesis releasably secured to the inner cannula, the prosthesis having a radially-inwardly contracted delivery configuration and a radially-expanded deployed configuration. The prosthesis comprises at least two suture loops secured to an outer surface of the prosthesis and circumferentially spaced from each other. A a releasable trigger wire extends along at least a portion of the length of the prosthesis, wherein the releasable trigger wire is wound around at least a portion of the inner cannula and wherein the releasable trigger wire engages at least one of the at least two suture loops to retain the prosthesis in the radially-inwardly contracted delivery configuration.

In one example, the prosthesis is a stent graft comprising biocompatible graft material.

In one example, the stent graft comprises at least one stent secured to the graft material, the at least one stent comprising at least one proximal apex and at least one distal apex and wherein the trigger wire engages at least one of the proximal stent apex and distal stent apex.

In one example, the stent graft comprises at least one stent secured to the graft material, the at least one stent comprising at least one proximal apex and at least one distal apex and at least one strut connecting said proximal apex to said distal apex, and wherein at least one of the at least two suture loops engages at least a portion of said strut.

In one example the trigger wire weaves in and out of the graft material.

In one example, the trigger wire is configured to both reduce the circumference of a prosthesis and releasably attach the prosthesis to the inner cannula.

In one example, the trigger wire comprises a tightened condition and a relaxed condition.

In one example, the trigger wire is in the tightened condition, the circumference of the prosthesis is reduced.

In one example, when the hybrid trigger wire is in the relaxed condition, the circumference of the prosthesis is enlarged.

In one example, the prosthesis has a first circumference when in radially-inwardly contracted delivery configuration and a second circumference when in a radially-expanded deployed configuration, wherein the second circumference is greater than the first circumference.

In one example, one of the at least two suture loops comprises a first suture loop and a second suture loop and wherein the first suture loop is threaded through the second suture loop.

In one example, the trigger wire extends through the first suture loop.

In one example, the trigger wire extends through the graft material and into a graft lumen, wraps around a portion of the inner cannula, extends back through the graft material to exit the graft lumen and extends through at least one of the at least two suture loops.

In one example, the trigger wire is helically wound around at least a portion of the inner cannula.

In one example, the trigger wire is helically wound around the inner cannula at least 2 times.

In one example, at least four suture loops are secured to an outer surface of the prosthesis, and wherein at least two suture loops are circumferentially spaced from each other and wherein at least two suture loops are longitudinally spaced from each other on the stent graft.

In one example, the at least two suture loops are longitudinally spaced apart a distance in the range of about 10 mm to about 40 mm along the body of the stent graft.

BRIEF DESCRIPTIONS OF THE DRAWINGS

FIG. 1 shows a longitudinal cross-sectional view of an exemplary delivery system for deploying a prosthesis within a body vessel.

FIG. 2 shows the delivery system of FIG. 1 with a prosthesis in a reduced diameter configuration after an introducer sheath has been withdrawn.

FIG. 3 shows an enlarged view of the releasable diameter reducing tie arrangement of FIG. 2.

FIG. 4 shows a cross-sectional view of the releasable diameter reducing tie arrangement of FIG. 2.

FIG. 5 shows a cross-sectional view of the releasable diameter reducing tie arrangement of FIG. 4 after the trigger wire has been withdrawn.

FIG. 6 shows a cross-sectional view of the releasable diameter reducing tie arrangement of FIG. 2.

FIG. 7 shows the delivery system of FIG. 2 with the prosthesis in a partially radially outwardly expanded configuration.

FIG. 10 shows a longitudinal cross-sectional view of an exemplary delivery system for deploying a prosthesis within a body vessel.

FIG. 11 shows an enlarged view of the releasable diameter reducing tie arrangement of FIG. 10.

DETAILED DESCRIPTION

Figure 8:
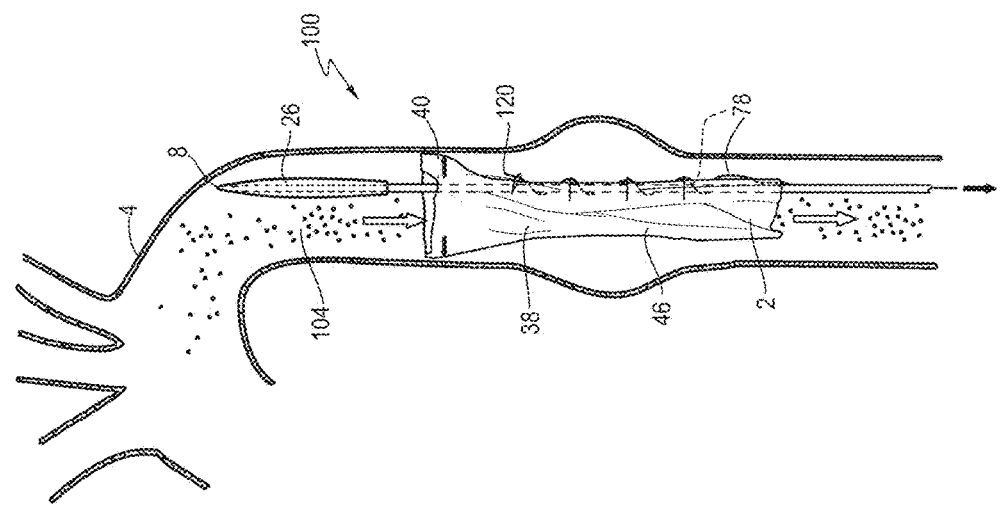
FIG. 8 shows one example of a delivery system in a vessel during a procedure.

The present disclosure relates to apparatus and methods for delivering and deploying endoluminal prostheses in a body vessel, duct, or lumen. In the present disclosure, the term "proximal" refers to a direction that is generally closest to the heart during a medical procedure, while the term "distal" refers to a direction that is farthest from the heart or other target tissue or organ during a medical procedure.

As used herein, the term "trigger wire" refers to an elongated, slender filament, wire and/or strand. In one example, a trigger wire may be comprised of metal, plastic or other polymers, usually having a generally circular or round cross-sectional shape, and used to at least partially restrain a portion of a prosthesis on a deployment device. In one example, a trigger wire may be made of Nitinol or stainless steel.

FIG. 1 shows a longitudinal cross-sectional view of an exemplary delivery system 100 for deploying a prosthesis 2 within a body vessel 4. Although the delivery system 100 is shown in the aorta, it may be used in any vessel, duct, or lumen.

Delivery system 100 includes an introducer 6 for delivering a prosthesis 2, such as an endovascular stent graft 38, stent, occlusion device, or any other implant to a body vessel 4. The introducer 6 has a proximal end 8 and a distal end (not shown in FIG. 1). The distal end of the introducer may include an external manipulation section or handle (not shown) that remains outside of the patient during a procedure that can be gripped and manipulated by a user.

The prosthesis 2 may be in a collapsed configuration or an expanded configuration. In the collapsed configuration (see FIG. 1), the prosthesis 2 has a reduced-diameter delivery state allowing it to maintain a relatively slender profile to be delivered to a target location within a vessel or duct. The prosthesis 2 also has an expanded deployed state in which it applies a radially outward force upon at least a portion of a vessel, duct, or lumen, e.g., to maintain patency within a passageway.

As shown in FIG. 1, the prosthesis 2 may be held in a radially inwardly or collapsed configuration within the delivery system 100 by a retractable introducer sheath 10 that is disposed about the prosthesis 2. Sheath 10 may have a proximal end 12, a distal end (not shown in FIG. 1), and a lumen 14 extending therebetween. The sheath 10 may be comprised of a flexible or pliable materials such as rubbers, plastics, polymers, including but not limited to PTFE, Nylon, Coiled or Braided Stainless Steel, PEBA, silicone or urethane.

The introducer 6 may also include an inner cannula 16 that may extend from the proximal end 8 to the distal end (not shown) of the introducer 6. The inner cannula 16 may be disposed coaxially within the lumen 14 of the sheath 10. The inner cannula 16 has a proximal end 18, a distal end (not shown), and an inner cannula lumen 20 extending there between. The inner cannula lumen 20 may be configured to receive a guide wire (not shown) therethrough to facilitate navigation of the introducer 6 within the vasculature.

A nose cone dilator 26 may be disposed at the proximal end 18 of the inner cannula 16. The inner cannula 16 may extend to a tapered proximal tip 28 of the nose cone dilator 26. For example, the nose cone dilator 26 may have a long forward taper 30 and a shorter reverse taper 32. The proximal tip 28 and long forward taper 30 presents an atraumatic surface to effectively navigate through a vessel lumen. Further, the reverse taper 32 presents an atraumatic surface to prevent the nose cone dilator 26 from snagging or catching on the prosthesis 2 or other parts of the delivery system 100 such as during distal withdrawal of the inner cannula 16 following deployment.

In one example, one or more trigger wires may be used to position stent graft(s) after the initial release from a deployment device. One such example is trigger wire 78 having a proximal end 102 and a distal end (not shown) is illustrated in FIG. 1. Trigger wire 78 may retain the prosthesis 2 in a particular configuration during delivery of the prosthesis 2. More specifically, trigger wire 78 may be a wire that is wound generally in a spiral configuration to secure the graft to the inner cannula 16 which runs through the graft lumen and, in addition, the trigger wire 78 may also secure a diameter reducing tie arrangement (described below) such that two points on the circumference of a stent graft 38 are held closer together, effectively reducing the diameter of the stent graft 38. As such, trigger wire 78 may be referred to hereafter as "hybrid trigger wire 78" because it is configured to accomplish at least these two functions, which will be described in greater detail below.

FIG. 2 shows a portion of the delivery system of FIG. 1 with a prosthesis in a reduced diameter configuration after an introducer sheath has been withdrawn. In one example, the prosthesis 2 may be a generally tubular stent graft 38 having a proximal end 40 and distal end 42 and a lumen 44 extending therethrough.

The stent graft 38 may be any suitable length corresponding to a length of the lesion site at which the stent graft is to be positioned. The stent graft 38 may be any suitable selected diameter and may be constructed of any biocompatible graft material 46 which is suitable for facilitating repair of an injured or diseased body vessel. The graft material 46 may be synthetic and/or naturally-derived material. Synthetic biocompatible polymers may include but are not limited to polyethylene terephthalate, polyurethane, nylon, polyester, high molecular weight polyethylene, polytetrafluoroethylene, or combinations thereof. The graft material 46 can be porous or non-porous and also may be impregnated or coated with one or more therapeutic substances. In one example, the graft material 46 may be constructed of the commercially available material referred to as Dacron. The graft material 46 may have openings or fenestrations (not shown) formed therein for providing fluid access to branch vessels, such as the renal arteries. The graft material 46 should have sufficient flexibility to allow for navigation of the vasculature and delivery to a targeted area in the body. Preferably, the graft material 46 is a low profile material or an ultralow profile material.

One or more stents 48 may be located on an interior surface 50, exterior surface 52, or both of the stent graft 38. For example, as illustrated in FIG. 2, stent segment 54 is located on the interior surface 50 of the stent graft 38. In one example, a plurality of stent segments 56, 58, 60, 62 are located on the exterior surface 52 of the stent graft 38. Stent segments 54, 56, 58, 60, 62 may have a distal end 64 with a series of distal apices 66 and a proximal end 68 with a series of proximal apices 70. Stent segments 54, 56, 58, 60, 62 may also have one or more elongate struts 71 connecting the distal apices 66 to the proximal apices 70. Alternatively, the stent graft 38 may be unsupported along its length such that there are no body stents located on the graft material 46 between the proximal and distal ends 40, 42 of the stent graft 38.

Suitable stents 48 for use in connection with the stent graft 38 described herein may be self-expanding or mechanically-expandable stents or both, and may be deployed according to conventional methodology. A self-expanding stent may be manufactured from a shape-memory alloy, such as nickel titanium alloy (Nitinol). If the stent comprises a self-expanding material such as Nitinol, the stent may be heat-set into the desired expanded state whereby the stent can assume a relaxed radially expanded configuration. The stent may be made from other metals and alloys that allow the stent to return to its original expanded configuration upon deployment, such as, for example, stainless steel, cobalt-chrome alloys, amorphous metals, and/or non-metallic materials as would be recognized by one of skill in the art. Additionally or alternatively, the stent graft 38 may be mechanically expanded, such as through the use of an expandable balloon placed within the lumen 44 of the stent graft 38 and then radially outwardly expanded to thereby expand the stent graft 38.

The prosthesis 2 may be anchored to an interior wall surface of a body vessel proximally and/or distally to a lesion site. For example, a proximal end 72 of the prosthesis 2 may be anchored to a main vessel wall proximal to an aneurysm. The proximal end 72 of the prosthesis 2 may include an anchor. Suitable anchors include any means for attaching a prosthesis 2 to a body vessel wall. In one example, one or more internal stent segments 54 at the proximal end 40 of the stent graft act to attach the graft 38 to the vessel by applying external pressure from the internal stent segment 54 to a vessel wall (not shown in FIG. 2). In another example, an anchor may be attached or adhered to the proximal end 72 of the prosthesis 2 by any means, including but not limited to welding, stitching, bonding, and adhesives. In one example, the anchor comprises a bare fixation stent (not shown) which may include barbs (not shown) attached to the proximal end 72 of the prosthesis 2.

The stent graft 38 can be expanded into the deployed configuration when the sheath 10 is withdrawn or retracted longitudinally in a distal direction. With the sheath 10 at least partially retracted to expose at least a portion of the stent graft 38, the stent graft 38 can radially expand.

Alternatively or in addition to a sheath 10, one or more mechanisms may be further provided for retaining one or both ends of the stent graft 38 in a diameter-reduced configuration and for securing the stent graft 38 to the introducer 6, including, but not limited to, diameter reducing ties, trigger wires, sutures and the like which would require removal before the stent graft 38 is permitted to fully expand and deploy. In one example, the prosthesis 2 can be temporarily retained on the delivery device by a releasable diameter reducing tie arrangement 80. For the diameter reducing tie arrangement 80, one or more hybrid trigger wires 78, together with one or more diameter reducing ties 84, 86 (described in more detail below), retain the graft material 46 of the prosthesis 2 and/or retain one or more stents 48 in a radially-inward contracted condition to achieve a reduction in the circumference of the prosthesis 2 and to provide axial fixation on the inner cannula.

Furthermore, the prosthesis 2 can also be temporarily retained on the delivery device by a spirally-wrapped wire arrangement ("spiral wire arrangement") 82. More specifically, the prosthesis 2 may be releasably retained and held in a reduced diameter delivery configuration on the inner cannula 16 by one or more trigger wires 78, which, in one example, may be spirally-wrapped, which prevent the prosthesis 2 from moving or dislodging from the inner cannula 16 during delivery until the sheath is withdrawn and the trigger wire 78 is removed. For example, the stent graft 38 may be retained on the inner cannula 16 by a hybrid trigger wire 78 until the trigger wire is removed by manual user operation, as described more fully below.

FIGS. 1-11 show one example of a hybrid trigger wire system 76 for a prosthesis 2. The hybrid trigger wire system 76 comprises a single hybrid trigger wire 78 that may serve both of the releasable retaining functions identified above. For example, a hybrid trigger wire system 76 may include one or more hybrid trigger wires 78 that function both as a (1) spiral wire arrangement 82 and also as (2) a releasable diameter reducing tie arrangement 80. In other words, a single hybrid trigger wire 78 may act as a spiral wire to secure the graft 38 to a cannula 16 which runs through the graft lumen 44. In addition, the single hybrid trigger wire 78 can hold a releasable diameter reducing tie arrangement 80 such that two points on the circumference of a stent graft 38 are held closer together, effectively reducing the diameter of the stent graft 38 as described in greater detail below.

As shown in exemplary FIGS. 2-6, a releasable diameter reducing tie arrangement 80 comprises at least two suture loops 84, 86 circumferentially spaced at a selected distance from each other on the graft material 46. The suture loops 84, 86 are arranged into a pair and may engage one another. As FIG. 6 shows, plurality of diameter reducing loop pairs 88, 90, 92, 94 may occur at selected spaced-apart longitudinal distances on the graft material 46. There may be more pairs of suture loops or fewer depending on various factors, including the length of the graft 38. The pairs of suture loops may be longitudinally spaced from each other along the length of the stent graft 38 and the distances between the loop pairs may be constant or they may vary. For example, the distance between suture loop pairs 88 and 90 at the proximal end of the stent graft may be closer together than the pairs of suture loops located near the distal end of the graft.

In a non-limiting example, the pairs of suture loops 88, 90, 92, 94 may be longitudinally spaced apart a distance being in the range of about 10 mm to about 40 mm along the body of the stent graft. The suture loops 84, 86 may be located anywhere along the length of the graft 38. In one example, suture loops 84, 86 are located in between one or more stent segments. In another example (shown in FIGS. 10-11) suture loops 84, 86 may be located about strut 71 of a stent 48. In particular, the suture loops 84, 86 may be tied about the center of strut 71 of a stent 48. In that way, when the suture loops 84, 86 are pulled closer together by the hybrid trigger wire 78, the stent struts 71 are also pulled closer together, reducing the diameter of the stent 48.

In one example, the suture loops 84, 86 may be constructed of thread, yarn, monofilament or braided suture, or other filamentous material that is durable, flexible and strong enough to resist breakage when tensile force is applied to it. The suture loops may be made of natural or synthetic fibers or combinations thereof.

FIG. 3 shows a close-up view of the releasable diameter reducing tie arrangement 80 of FIG. 2. In one example, suture loops 84 and 86 are attached to tubular stent graft material 46 and circumferentially spaced apart. One loop 84 may be looped or threaded into the other loop 86 of the pair and one or both suture loops may be temporarily held in place with the hybrid trigger wire 78.

As shown in FIG. 4, hybrid trigger wire 78 is passed through at least one suture loop 86. In a non-limiting example, it may be advantageous to thread one suture loop through the other suture loop and then have the hybrid trigger wire extend through only one of the suture loops as shown in FIGS. 3 and 4 to reduce the likelihood that the suture loops would slide longitudinally away from each other along the hybrid trigger wire 78. If the suture loops 84, 86 were to slide longitudinally away from each other, the circumference of the graft may inadvertently and/or prematurely begin to expand. By threading one of the suture loops through the other as shown in FIGS. 3 and 4 and then securing this position with the hybrid trigger wire 78, one loop is prevented from sliding or migrating away from the other loop because they are engaged. Alternatively, the suture loops may interact in other ways. For example, suture loops 84, 86 may overlap such that the hybrid trigger wire 78 is threaded through both suture loops 84 and 86.

When the stent graft 38 is in the delivery configuration, the hybrid trigger wire 78 extends longitudinally along the tubular graft material 46 and engages with one or more of the suture loops of thread 84, 86. As shown in FIG. 3, the hybrid trigger wire 78 passes through loop 86 to secure the diameter reducing tie arrangement 80. When hybrid trigger wire 78 is tightened, it pulls suture loops 84, 86 closer. As a result, the graft material 46 is pulled inwardly and closer together and the diameter of the graft 38 is thereby reduced. In one example, the graft material 46 may be pulled together such that the diameter of the stent graft in a radially-inwardly contracted delivery configuration is in the range of 10 mm to about 40 mm.

FIG. 5 shows one example of a cross-sectional view of the releasable diameter reducing tie arrangement 80 of FIG. 4 when the hybrid trigger wire 78 has been withdrawn. FIG. 5 illustrates suture loops 84 and 86 may be attached to tubular stent graft material 46. When the hybrid trigger wire 78 (not shown in FIG. 5) is removed from the releasable diameter reducing tie arrangement 80, suture loops 84 and 86 are released and allow the stent graft to assume a radially-expanded configuration. In other words, the stent graft 38 is no longer held in a reduced diameter configuration due to the hybrid trigger wire 78 having been removed.

In one example, FIG. 2 illustrates that the spiral wire arrangement 82 may be configured to achieve greater accuracy of rotational alignment and/or maintain greater degree of control over the stent graft 38 during deployment. In one example, hybrid trigger wire 78 releasably secures the stent graft 38 to the inner cannula 16 which runs longitudinally through the lumen 44 of the stent graft 38. When the stent graft 38 has been delivered and placed in a desired location within a vessel, the hybrid trigger wire 78 may be released so that the stent graft is no longer secured to the inner cannula by the hybrid trigger wire 78. One example of a stent graft introducer incorporating a spiral wire retention system is disclosed in U.S. Pat. No. 8,864,808 filed on Sep. 21, 2006 and entitled "Endoluminal Delivery Assembly" which is incorporated by reference herein in its entirety.

FIG. 6 shows a cross-sectional view of the releasable diameter reducing tie arrangement of FIG. 2. In one example, hybrid trigger wire 78 extends from the release mechanism (not shown) on distal manipulation portion of the delivery device handle (not shown) and through the lumen 20 of the inner cannula 16. As shown in FIG. 2, and in greater detail in FIG. 6, the hybrid trigger wire 78 exits the inner cannula lumen 20 through a fenestration 96 that may be distal to the distal end 42 of the stent graft 38. The hybrid trigger wire 78 can extend outside of the stent graft 38 and extend through one or more suture loops 84, 86 of the diameter reducing tie arrangement system 80. In addition, the hybrid trigger wire 78 may capture the distal apex 66 of a stent 48 before extending through the graft material 46 into the lumen 44 of the stent graft 38 The hybrid trigger wire 78 may helically wrap around at least a portion of the inner cannula 16 and go back up through the graft material 46 to the outside of the stent graft 38, where it may pass through another suture loop 86 and capture another distal apex 66 of a stent 48. The hybrid trigger wire 78 may go back through the graft material 46 to the inside lumen 44 of the stent graft 38 and wrap helically around another portion of the inner cannula 16. This process may be repeated several times along the length of the stent graft 38. In one non-limiting example, the hybrid trigger wire 78 may be helically wrapped around the inner cannula 16 anywhere between 2 times and 11 times along the length of the stent graft 38.

The proximal end 102 of the hybrid trigger wire 78 may be releasably secured to the proximal end 8 of introducer 6. For example, the proximal end 102 of hybrid trigger wire 78 may be releasably retained on the introducer 6 by friction fit between an internal surface of the nose cone dilator 26 and an outer surface of the inner cannula 16. Alternatively, as shown in FIG. 6 the proximal end 102 of the hybrid trigger wire 78 may be inserted into and secured within a portion of the lumen 20 of the inner cannula 16.

One hybrid trigger wire 78 may be used with a delivery system. In other words, the hybrid trigger wire 78 used with the diameter reducing tie arrangement 80 can be the same hybrid trigger wire 78 used with the spiral wire arrangement 82. In this way, one hybrid trigger wire 78 could replace a delivery system containing multiple trigger wires and/or diameter reducing ties. Therefore, a hybrid trigger wire 78 as described above can reduce the amount of trigger wires within a delivery system. A delivery system using a hybrid trigger wire 78 (and reducing the number of trigger wires in a delivery system) reduces the likelihood of multiple wires interacting with one another or other components of the delivery system and becoming twisted or difficult to remove, thereby resulting in a procedure having decreased complexity and procedure length. In addition, having a single hybrid trigger wire 78 instead of multiple trigger wires will decreases the time and complexity associated with the manufacture, assembly, and loading of the delivery device.

Once the stent graft 38 is located in the desired area of a vessel and the sheath 10 is withdrawn, the stent graft 38 can then be expanded and released from the inner cannula 16 by removing the hybrid trigger wire 78. Removal of the hybrid trigger wire 78 releases the spiral wrap configuration of the wire 78 that held the stent graft 38 on to the inner cannula 16 and also releases the diameter reducing ties 84, 86 allowing the stent graft to release from the inner cannula 16 and radially-outwardly expand to engage the vessel wall. The hybrid trigger wire 78 can be removed by withdrawing the hybrid trigger wire 78 distally with sufficient force so that the proximal end 102 of the hybrid trigger wire 78 is released from the inner cannula 16 (and/or released from any other attachment mechanism that may have retained the proximal end 102 of the hybrid trigger wire 78).

FIG. 7 shows one example of the delivery system of FIG. 2 with the prosthesis in a partially radially outwardly expanded or deployed configuration. As the hybrid trigger wire 78 is withdrawn distally, the proximal end 40 of the stent graft 38 is released and can expand circumferentially. As illustrated in FIG. 7, the proximal end 102 of the hybrid trigger wire 78 has been pulled distally such that it is released from the inner cannula 16. The trigger wire 78 has moved distally enough to release suture loops 84, 86 so that the diameter-reducing tie arrangement 80 is no longer holding that portion of the stent graft in a radially-inwardly contracted condition against the inner cannula 16. As such suture loops 84 and 86 become disengaged and that segment of the stent graft 38 is no longer held in a diameter-reduced configuration.

Figure 9:
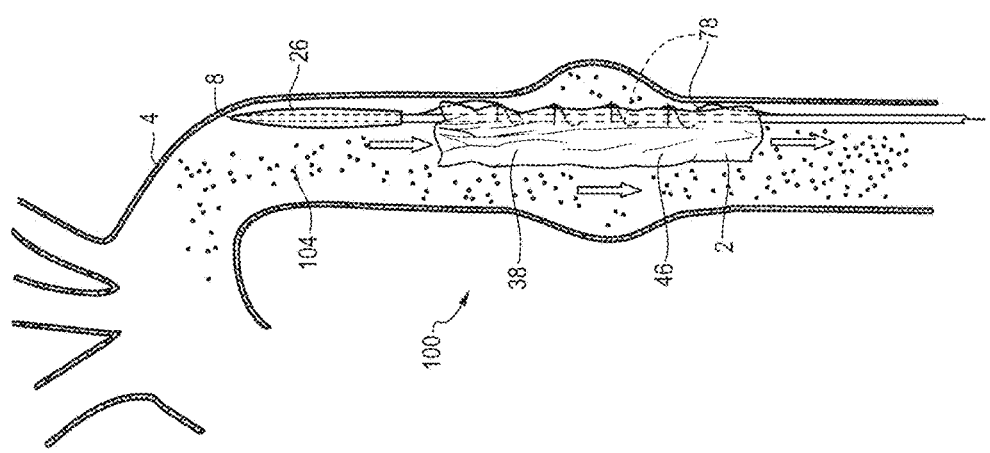
FIG. 9 shows one example of a delivery system in a vessel during a procedure.

FIG. 8 shows one example of the delivery system of FIG. 2 in a vessel 4. After the introducer sheath has been withdrawn, but while the hybrid trigger wire 78 is still holding the stent graft 38 in a diameter reduced configuration, blood 104 may begin to flow into lumen 44 of the stent graft 38. The hemodynamic force created by the flow of blood through the lumen 44 of the prosthesis 2 serves to at least partially expand the prosthesis 2 within the vessel. FIG. 9 shows the delivery system of FIG. 7 in a vessel 4. As the hybrid trigger wire 78 is withdrawn distally, the proximal end 40 of the stent graft 38 is unconstrained and can expand circumferentially to engage the vessel wall.

The aforementioned hybrid trigger wire 78 may be used in any suitable method of delivery of a stent graft or other prosthesis. In one example, the hybrid trigger wire takes a relatively longitudinal path along the graft (although the path could be somewhat oblique), passing over each stent on the exterior of the graft, then passing back through the graft material to the interior and looping around the shaft of the inner cannula before passing back through the graft material to the exterior to cross over the next stent. At each stent, a suture loop (such as suture loops 84, 86) may be tied to a stent strut 71 (as shown in FIGS. 10-11) and/or graft material 46 (shown in FIGS. 3-4) some distance on either side of the hybrid trigger wire path. As the hybrid trigger wire passes over each stent, one suture loop 86 is pulled through the other loop 84, pulling the two struts to which the suture loops are tied closer together, and creating a loop through which the hybrid trigger wire 78 can pass and secure the diameter reduction. This can be done at one or several points along the hybrid trigger wire path. A hybrid trigger wire 78 could also be configured to serve additional diameter-reducing or stent graft-securing functions concurrently with the functions detailed above. Such functions could include one or multiple proximal tie downs to secure the proximal end of the graft to a delivery system tip, or distal ties to secure the graft to a delivery system supporting core.

While various embodiments of the invention have been described, the invention is not to be restricted except in light of the attached claims and their equivalents.

We claim:

1. An endovascular prosthesis delivery system comprising:
    an inner cannula;
    a prosthesis comprising graft material releasably secured to the inner cannula, the prosthesis having a radially-inwardly contracted delivery configuration and a radially-expanded deployed configuration, wherein the prosthesis comprises at least two suture loops secured to an outer surface of the prosthesis and circumferentially spaced from each other;
    a releasable trigger wire extending along at least a portion of a length of the prosthesis, wherein the releasable trigger wire extends through the graft material and into a graft lumen, wraps around a circumference of the inner cannula, extends back through the graft material to exit the graft lumen and extends through at least one of the at least two suture loops to retain the prosthesis in the radially-inwardly contracted delivery configuration.

2. The prosthesis delivery system of claim 1, where in the prosthesis is a stent graft comprising biocompatible graft material.

3. The prosthesis delivery system of claim 2, wherein the stent graft comprises at least one stent secured to the graft material, the at least one stent comprising at least one proximal apex and at least one distal apex and wherein the trigger wire engages at least one of the proximal stent apex and distal stent apex.

4. The prosthesis delivery system of claim 2, wherein the stent graft comprises at least one stent secured to the graft material, the at least one stent comprising at least one proximal apex and at least one distal apex and at least one strut connecting said proximal apex to said distal apex, and wherein at least one of the at least two suture loops engages at least a portion of said strut.

5. The prosthesis delivery system of claim 2, wherein the trigger wire weaves in and out of the graft material.

6. The prosthesis delivery system of claim 2, wherein at least four suture loops are secured to the outer surface of the prosthesis, and wherein at least two suture loops are circumferentially spaced from each other and wherein at least two suture loops are longitudinally spaced from each other on the stent graft.

7. The prosthesis delivery system of claim 2, where the at least two suture loops are longitudinally spaced apart a distance in the range of about 10 mm to about 40 mm along a body of the stent graft.

8. The prosthesis delivery system of claim 1, wherein the trigger wire is configured to both reduce the circumference of the prosthesis and releasably attach the prosthesis to the inner cannula.

9. The prosthesis delivery system of claim 1, wherein the trigger wire comprises a tightened condition and a relaxed condition.

10. The prosthesis delivery system of claim 9, wherein when the trigger wire is in the tightened condition, a circumference of the prosthesis is reduced.

11. The prosthesis delivery system of claim 9, wherein when the trigger wire is in the relaxed condition, a circumference of the prosthesis is enlarged.

12. The prosthesis delivery system of claim 1 wherein the prosthesis has a first circumference when in the radially-inward contracted delivery configuration and a second circumference when in a radially-expanded deployed configuration, wherein the second circumference is greater than the first circumference.

13. The prosthesis delivery system of claim 1, wherein one of the at least two suture loops comprises a first suture loop and a second suture loop and wherein the first suture loop is threaded through the second suture loop.

14. The prosthesis delivery system of claim 13, wherein the trigger wire extends through the first suture loop.

15. The prosthesis delivery system of claim 1, wherein the trigger wire is helically wound around at least a portion of the inner cannula.

16. The prosthesis delivery system of claim 15, wherein the trigger wire is helically wound around the inner cannula at least 2 times.

17. An endovascular prosthesis delivery system comprising:
an inner cannula;
a prosthesis comprising graft material releasably secured to the inner cannula, the prosthesis having a radially-inwardly contracted delivery configuration and a radially-expanded deployed configuration, wherein the prosthesis comprises at least one pair of suture loops secured to an outer surface of the prosthesis and circumferentially spaced from each other;
a releasable trigger wire extending along at least a portion of a length of the prosthesis, wherein the releasable trigger wire extends through the graft material and into a graft lumen, wraps around a circumference of the inner cannula within the lumen, extends back through the graft material to exit the graft lumen and extends through at least one of the pairs of suture loops to retain the prosthesis in the radially-inwardly contracted delivery configuration.

18. The endovascular prosthesis delivery system of claim 17, wherein the releasable trigger wire extends through the graft material and into the graft lumen, wraps around a portion of the inner cannula within the lumen, extends back through the graft material to exit the graft lumen and extends through a first pair of the at least one pair of suture loops to retain the prosthesis in the radially-inwardly contracted delivery configuration.

19. The endovascular prosthesis delivery system of claim 17, wherein the at least one pair of suture loops comprises a plurality of pairs of suture loops extending a length of an exterior of the graft and the releasable trigger wire extends through the graft material and into the graft lumen, wraps around a portion of the inner cannula within the lumen, extends back through the graft material to exit the graft lumen and extends through a first pair off the at least one pair of suture loops, extends through the graft material and into the graft lumen, wraps around a second portion of the inner cannula within the lumen, extends back through the graft material to exit the graft lumen and extends through a second pair of the at least one pair of suture loops to retain the prosthesis in the radially-inwardly contracted delivery configuration.

20. The endovascular prosthesis delivery system of claim 19, where in the releasable trigger wire helically wraps around a portion of the inner cannula from a first end of the prosthesis to a second end of the prosthesis.

* * * * *

UNITED STATES PATENT AND TRADEMARK OFFICE
CERTIFICATE OF CORRECTION

PATENT NO. : 10,188,538 B2
APPLICATION NO. : 14/984048
DATED : January 29, 2019
INVENTOR(S) : Derek Eller et al.

Page 1 of 1

It is certified that error appears in the above-identified patent and that said Letters Patent is hereby corrected as shown below:

On the Title Page

Inventors:
In (72), second inventor, please replace "Saylon" with –Saylan–.

Signed and Sealed this
Twenty-first Day of April, 2020

Andrei Iancu
*Director of the United States Patent and Trademark Office*